United States Patent [19]

Osypka et al.

[11] Patent Number: 4,633,880
[45] Date of Patent: Jan. 6, 1987

[54] SURGICAL ELECTRODE

[75] Inventors: Peter Osypka, Hornrain 31, D-7889 Grenzach-Wyhlen; Rüdiger Höge, Giessen, both of Fed. Rep. of Germany

[73] Assignee: Peter Osypka, Grenzach-Wyhlen, Fed. Rep. of Germany

[21] Appl. No.: 719,901

[22] Filed: Apr. 4, 1985

[30] Foreign Application Priority Data

Apr. 6, 1984 [DE] Fed. Rep. of Germany ....... 3412950

[51] Int. Cl.$^4$ .............................................. A61B 5/04
[52] U.S. Cl. ............................... 128/642; 128/303.18; 128/419 P; 128/785
[58] Field of Search ....................... 128/303.18, 303.19, 128/419 P, 642, 784, 785

[56] References Cited

U.S. PATENT DOCUMENTS

| 4,046,151 | 9/1977 | Rose | 128/785 |
| 4,374,527 | 2/1983 | Iverson | 128/785 |
| 4,530,368 | 7/1985 | Saulson et al. | 128/419 P |

FOREIGN PATENT DOCUMENTS 0083674 11/1982 European Pat. Off. .

OTHER PUBLICATIONS

"A New Design for ... Wire", by D. C. Syracuse et al., Annals of Biomedical Engineering, No. 4, Dec. 1977, pp. 362-365.

Primary Examiner—Kyle L. Howell
Assistant Examiner—Randy Citrin
Attorney, Agent, or Firm—Peter K. Kontler

[57] ABSTRACT

A surgical electrode which can be used as a temporary lead for cardiac pacing or monitoring purposes has two elongated conductors whose distal ends are provided with spaced-apart poles and are implanted in a single operation by means of a surgical needle which is separably secured to the distal end of one of the conductors. The proximal ends of the conductors are connected to an elongated extension which passes through and outwardly from the thorax to be connected to a pacemaker or to an instrument which makes electrocardiograms. The conductors are insulated from each other and that pole which is nearer to the needle is defined by one or more bare strands which have a zig-zag, undulate, helical and/or other shape allowing the strands to reduce the width of the respective pole during penetration into the heart wall. The strands thereupon tend to increase the width of the respective pole to ensure reliable retention of the pole in contact with the surrounding tissue as well as to prevent migration of the pole in the heart wall. The needle is severed from the corresponding conductor when the two poles are properly implanted. The conductor which defines the radially expandible and contractible pole extends through the pole of the other conductor and is clampingly engaged by that portion of the other conductor which defines the respective pole so as to ensure that the pole of the other conductor shares the movement of the expandible pole during implantation into the heart wall.

22 Claims, 10 Drawing Figures

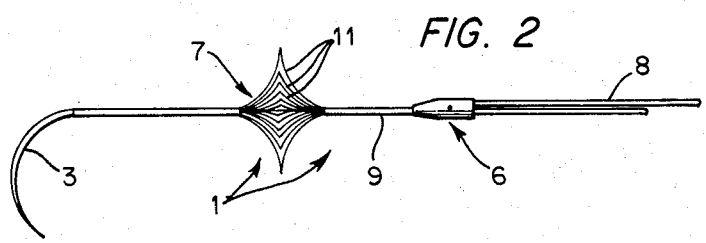
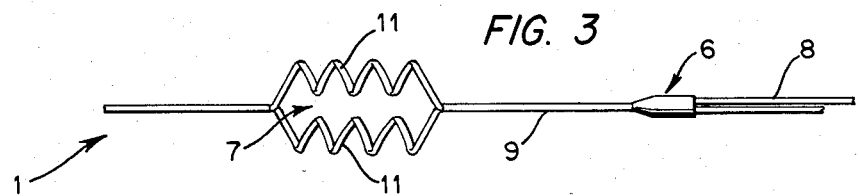
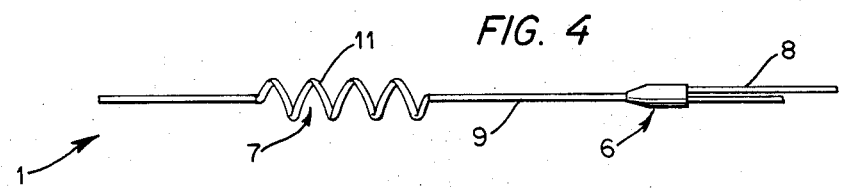
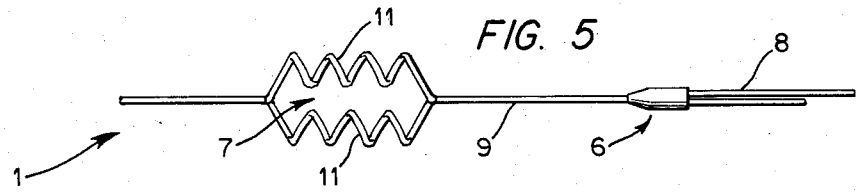
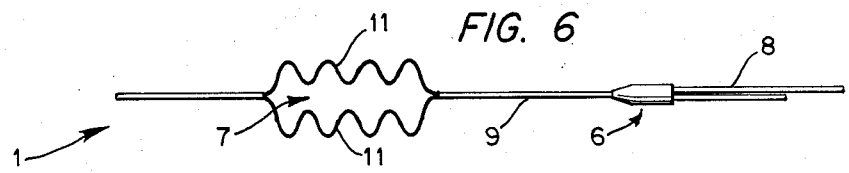
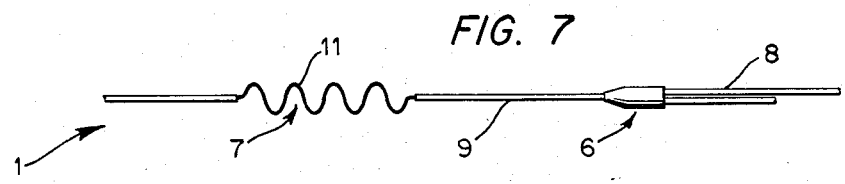
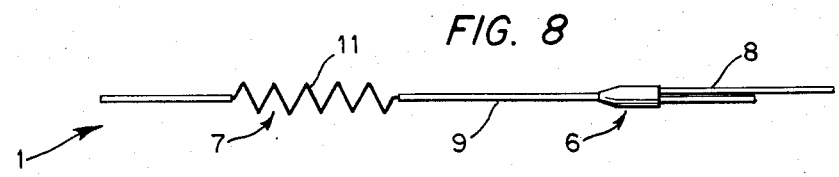
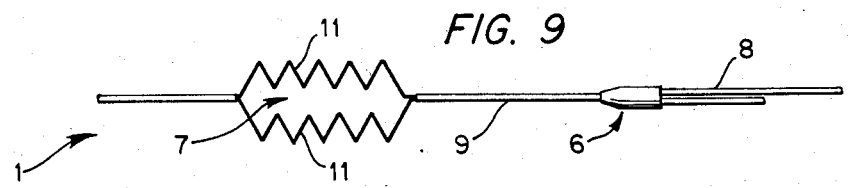

SURGICAL ELECTRODE

CROSS-REFERENCE TO RELATED CASES

Surgical electrodes are disclosed in the commonly owned copending patent application Ser. No. 541,389 and in the commonly owned U.S. Pat. No. 4,466,690.

BACKGROUND OF THE INVENTION

The present invention relates to improvements in surgical electrodes, especially in so-called temporary leads for cardiac pacing and monitoring purposes.

U.S. Pat. No. 4,010,756 discloses a heart pacer lead wire wherein the distal end of a conductor is connected with a separable needle serving to implant the pole of the conductor in the heart wall. The proximal end of the conductor extends through and outwardly from the thorax for attachment to a pacemaker. The conductor includes several strands of very thin stainless steel wire surrounded by a sheath consisting of synthetic plastic material which is not likely to be rejected by the body of the patient. The two end portions of the conductor are bare and the length of each of the bare end portions is in the range of 2 cm. The surgical needle (preferably a curved needle) is integral with but can be broken or severed away from the bare end portion at the distal end; the needle serves to implant the bare end portion (pole) at the distal end of the conductor into the myocardium and is thereupon separated from the distal end and removed from the body. The other bare end portion is at first secured to a straight surgical needle which is caused to penetrate through the thorax and establishes the electrical connection between the implanted pole and a pacemaker. This enables the latter to stimulate the heart in the event of disturbances of the rhythm. A second electrode is implanted in a similar manner to locate a second pole in the myocardium. The electrodes remain implanted for a period of two to three weeks and are thereupon extracted from the body.

A drawback of the just described and similar electrodes is that each pacing or monitoring operation necessitates the implantation of two discrete electrodes, i.e., the implantation of two discrete conductors by means of two discrete needles. Thus, the implantation of two electrodes (namely the introduction of two poles into the heart wall) necessitates the making of two punctures in the heart wall. This greatly increases the likelihood of accidental premature extraction of the one or the other electrode and renders it necessary to forestall such possibility by appropriate surgical undertakings. For example, the distal ends of the electrodes are slightly bent or a slight ligature is placed around each of the electrodes. It was also proposed to provide the distal ends of such electrodes with loops to facilitate their anchoring in the heart wall. All such undertakings are time-consuming, costly and necessitate additional penetration into the tissue of the heart.

Applicants are further aware of German Utility Model No. 70 47 748 which discloses a bipolar electrode for intravenous introduction into a cardiac cavity, of German Offenlegungsschrift No. 1,939,806 which discloses two unipolar electrodes and discrete needles, of German Offenlegungsschrift No. 28 46 136 which discloses a unipolar electrode, and of published European patent application No. 0 083 674 which discloses a unipolar electrode with a curved surgical needle.

OBJECTS AND SUMMARY OF THE INVENTION

An object of the present invention is to provide a surgical electrode which can be introduced into the body of a patient with lesser damage to the tissue than in connection with the implantation of conventional unipolar electrodes.

Another object of the invention is to provide an electrode which is designed to effect the implantation of several poles by means of a single surgical needle and in a single operation.

A further object of the invention is to provide an electrode which ensures that the implanted poles are located and remain at an optimum distance from one another.

An additional object of the invention is to provide an electrode which ensures predictable retention of at least one of the poles in a highly satisfactory contact with the tissue of the organ in which the poles are implanted.

Still another object of the invention is to provide a novel and improved method of implanting the poles of a temporary lead for cardiac pacing or monitoring purposes in the heart wall of a patient.

Another object of the invention is to provide novel and improved conductors for use in the above outlined surgical electrode.

A further object of the invention is to provide a surgical electrode which enhances the ability of the implanted conductor means to effect a desirable excitation at the locations of the poles.

An additional object of the invention is to provide a novel and improved connection between the conductors of a temporary lead for cardiac pacing or monitoring purposes.

One feature of the invention resides in the provision of a multipolar surgical electrode which can be used with particular advantage as a temporary lead for cardiac pacing or monitoring purposes. The improved electrode comprises a first elongated conductor having a proximal end and a distal end and including a first pole disposed at the distal end, a second elongated conductor which is electrically insulated from and extends along the first conductor and has a proximal end and a distal end adjacent the distal end of the first conductor and having a second pole spaced apart from the first pole, and a needle (preferably a curved surgical needle) which is secured to (e.g., integral with) the distal end of the first conductor and serves to effect simultaneous introduction of the two poles into the heart wall. The needle is preferably separable (e.g., breakable or severable away) from the distal end of the first conductor, and the improved electrode preferably further comprises an extension which is connected to the proximal ends of the two conductors and extends through and outwardly from the thorax of the patient whose heart wall receives the two poles.

The pole of the first conductor is nearer to the needle than the pole of the second conductor, and the pole of the first conductor is preferably defined by a deformable portion of the first conductor. The width of such deformable portion of the first conductor, as considered transversely of the first conductor, exceeds the average width of the first conductor (i.e., the diameter of the conductor if the latter is made of a single wire) and the width of the aforementioned deformable portion of the first conductor decreases during introduction of the respective pole into the heart wall whereupon the deformable portion tends to expand to thus establish a pronounced contact with the surrounding tissue. The deformable portion of the first conductor can have an undulate, helical, zig-zag or other uneven shape which allows for a reduction of the width of the deformable portion during introduction into the tissue. The deformable portion can consist of two or more discrete strands and at least one of these strands can have a zig-zag, undulate, helical or similar shape which contributes to increased width of the deformable portion.

The pole of the second conductor can be defined by a tubular member which conducts electric current, and the first conductor then preferably extends through and beyond the tubular member toward the needle. The distal end of the second conductor can be convoluted around the first conductor in the interior of the tubular member which latter is insulated from the first conductor. The tubular member can have an open proximal end and a hollow conical portion at the distal end. The first conductor extends into, through the tip of and beyond the conical portion of the tubular member.

The electrode preferably further comprises means for facilitating discrimination between the two conductors. For example, at least one of the conductors can be surrounded by a sheath having a particular color or another readily discernible characteristic. It is presently preferred to provide an insulating sheath for each of the two conductors and to use two differently colored, textured or otherwise readily distinguishable sheaths.

Another feature of the invention resides in the provision of a unipolar surgical electrode, particularly for use as a temporary lead for cardiac pacing or monitoring purposes. The electrode comprises an elongated electrical conductor having (a) a proximal end which is connected or connectable to the aforementioned extension, (b) a distal end and (c) a pole in the region of the distal end. The pole is defined by a deformable portion of the conductor and the width of such portion, as considered transversely of the conductor, exceeds the average width (e.g., diameter) of the conductor. The electrode further comprises a preferably curved surgical needle which is preferably separably secured to the distal end of the conductor and serves to effect implantation of the pole in the heart wall. The deformable portion preferably tends to assume an expanded shape and its width decreases during introduction into the heart wall but thereupon tends to increase so as to establish a pronounced contact with the adjacent tissue.

The novel features which are considered as characteristic of the invention are set forth in particular in the appended claims. The improved surgical electrode itself, however, both as to its construction and the mode of implanting the same, together with additional features and advantages thereof, will be best understood upon perusal of the following detailed description of certain specific embodiments with reference to the accompanying drawing.

BRIEF DESCRIPTION OF THE DRAWING

FIG. 2 is an enlarged elevational view of the distal ends of the two conductors, of their poles and of the needle;

FIG. 3 is an elevational view of the distal ends of the conductors in a modified electrode wherein the pole of the first electrode is defined by several helical strands;

FIG. 4 is a similar elevational view but showing the distal end of a first conductor wherein the pole is defined by a helically convoluted portion;

FIG. 5 illustrates the structure of FIG. 3 except that the helices of the strands defining the pole of the first conductor are inclined in opposite directions;

FIG. 6 illustrates a portion of a further electrode wherein the pole of the first conductor is defined by two undulate strands;

FIG. 7 illustrates a portion of an electrode wherein the pole of the first conductor is defined by a single undulate wire;

FIG. 8 illustrates a portion of another electrode wherein the pole of the first conductor is defined by a single zig-zag shaped wire;

FIG. 9 illustrates a portion of an additional electrode wherein the pole of the first conductor is defined by two zig-zag shaped strands.

DESCRIPTION OF THE PREFERRED EMBODIMENTS

Figure 1:
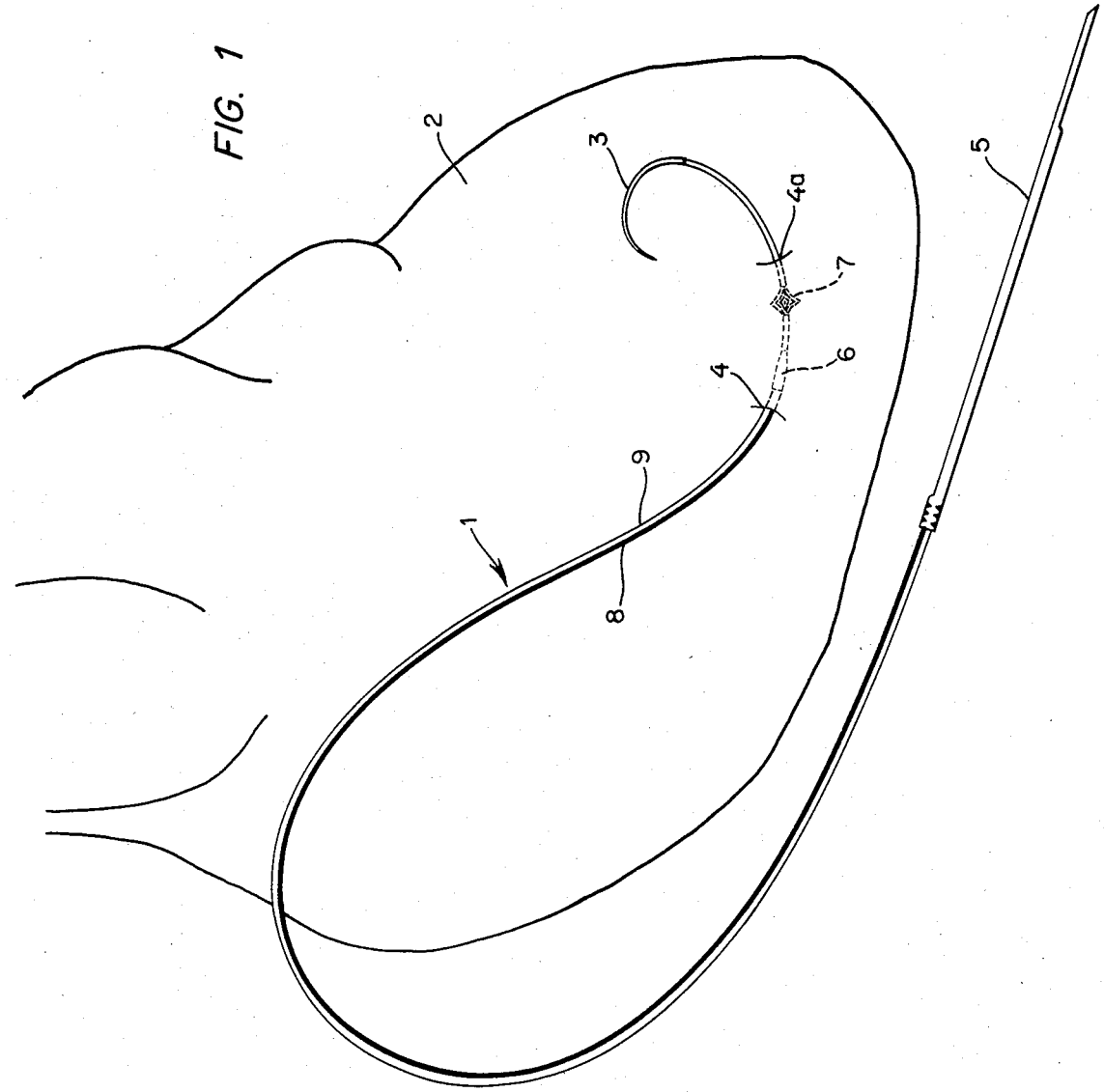
FIG. 1 is an elevational view of a bipolar surgical electrode with the poles of the two conductors implanted in the heart wall and the curved surgical needle disposed in the thorax preparatory to separation from the first conductor.

Referring first to FIG. 1, there is shown a surgical electrode 1 which comprises a first elongated flexible conductor 9 having a distal end which is implanted in the wall of the heart 2 of a patient and is separably connected to the rear end of a preferably curved surgical needle 3. The conductor 9 has a radially expandable and contractible pole 7 which is in contact with the tissue of the heart wall, and the proximal end of this conductor is secured to an elongated extension 5 which extends through and outwardly from the thorax of the patient to be connected with a cardiac pacemaker or with a monitoring device, e.g., an apparatus for making electrocardiograms. The electrode 1 further comprises a second conductor 8 which extends along the major part of the conductor 9, whose proximal end is connected to the extension 5 and whose distal end is provided with a pole 6 contacting the tissue of the heart wall rearwardly of the needle 3, i.e., the pole 7 of the conductor 9 is located between the pole 6 and the needle 3, as considered in the longitudinal direction of the electrode 1. The locus of penetration of the needle 3 into the heart wall for the purpose of temporarily implanting the poles 6 and 7 in the tissue of the heart wall is indicated at 4. The needle 3 exits from the heart wall at 4a and is thereupon separated (e.g., cut away) from the distal end of the conductor 9.

The poles 6 and 7 of the conductors 8 and 9 are spaced apart from one another, as considered in the longitudinal direction of the electrode 1, and the conductors 8 and 9 are electrically insulated from each other. In accordance with a feature of the invention, the distal end of the conductor 9 can actually extend through and beyond the pole 6 to define the pole 7 and to support the needle 3 or an analogous needle. The manner in which the conductor 9 can extend through the pole 6 of the conductor 8 is shown on a larger scale in FIG. 2 and on a much larger scale in FIG. 10.

The pole 7 is defined by a radially deformable portion of the conductor 9 close to its distal end. In FIG. 2, the conductor 9 includes a plurality of strands 11 which are separated from one another (each such strand can have a substantially V-shaped outline) so that the width of the pole 7 (as considered transversely of the longitudinal direction of the electrode 1 and its conductors 8, 9) exceeds the average width (e.g., diameter) of the conductor 9. The strands 11 tend to move apart but are caused to move nearer to each other (i.e., the width of the pole 7 decreases) during implantation of the pole into the heart wall. The strands 11 then tend to move apart and to establish a highly satisfactory contact with the surrounding tissue. It can be said that the deformable portion including the strands 11 of the conductor 9 constitutes an anchor which is reliably embedded in the heart wall when the needle 3 reaches the position of FIG. 1. In addition, the anchor effects a desirable superior excitation when the conductors 8, 9 are connected to a cardiac pacemaker.

FIG. 3 shows a portion of a modified electrode 1 wherein the strands 11 of the deformable portion of the conductor 9 define the pole 7 and constitute helices which are normally spaced apart from each other but move nearer to each other and also flatten out during introduction into the heart wall to thereupon tend to move apart and to thus increase the width of the deformable portion of the conductor 9. The helices of the two strands 11 are inclined in the same direction. It is clear that the pole 7 of the conductor 9 which is shown in FIG. 3 can be defined by more than two helical strands 11 or by a single helical strand as shown in FIG. 4. FIG. 5 shows the structure of FIG. 3 except that the two strands 11 define helices which are inclined in opposite directions.

FIG. 6 shows that the pole 7 of the conductor 9 is defined by two undulate strands 11, and FIG. 7 shows a pole 7 which is defined by a single undulate strand 11. As used herein, the term "undulate" is intended to embrace meandering, wavy, sinusoidal and/or similar shapes as well as the combinations thereof.

FIG. 8 illustrates a pole 7 which is defined by a single zig-zag shaped deformable portion 11 of the conductor 9, and FIG. 9 shows a pole 7 which is defined by several zig-zag shaped strands 11. The advantages of the deformable portions of the conductors 9 which are shown in FIGS. 3 to 9 are analogous to those of the strands 11 which are shown in FIG. 2, i.e., they ensure superior anchoring of the conductor 9 in the tissue of the heart wall, a more pronounced excitation effect and the ability to reduce their width so as to allow for implantation in the heart wall through a narrow channel which is formed by the needle 3 or an analogous needle.

It is clear that the deformable conductor portions 11 which are shown in FIGS. 2 to 9 can be used in a number of combinations with each other. For example, one strand 11 of a conductor 9 can constitute a helix and another strand of the same conductor 9 can have a zig-zag or undulate shape. Moreover, each of the strands 11 shown, for example, in FIG. 3 can include a single piece of wire-like material or two or more discrete wires which are twisted to form a composite strand. The strands 11 which define the pole 7 of FIG. 2 are deformed to a different extent (they can be said to form several sets with the sets of strands mirror symmetrical to one another). On the other hand, the strands which are shown in FIGS. 3, 5, 6 and 9 are deformed to the same extent. The elasticity of the strands 11 may but need not be so pronounced that they reassume their original shape when the implantation of the respective pole 7 in the tissue of the heart wall is completed.

Figure 10:
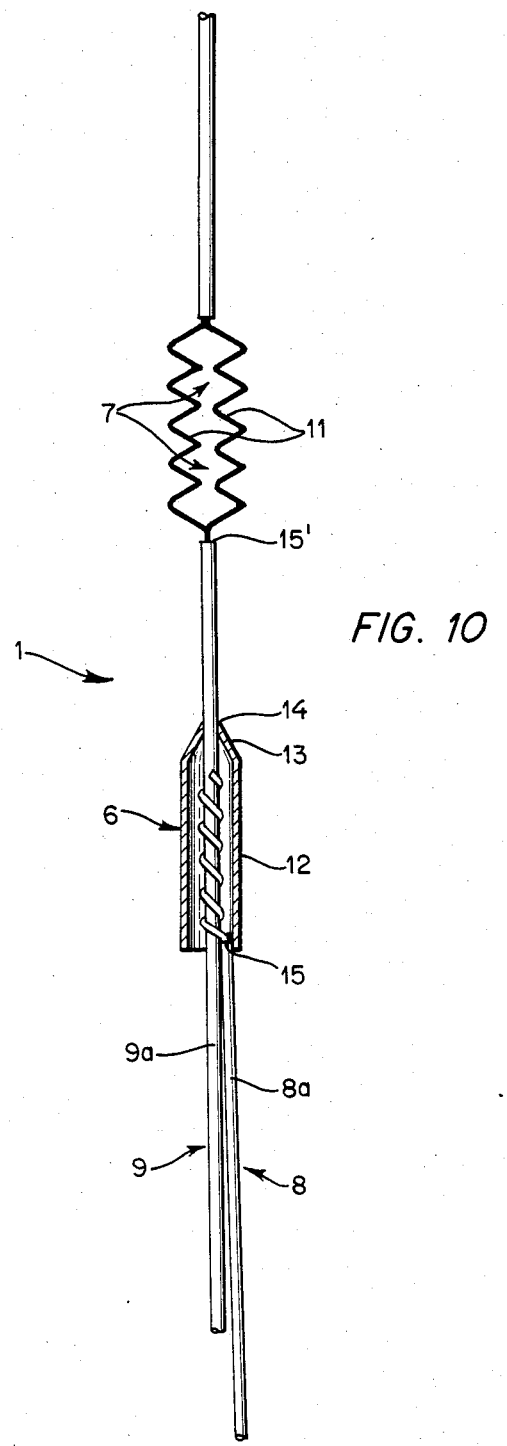
FIG. 10 is an enlarged view of the structure which is illustrated in FIG. 9, with the pole of the second conductor shown in an axial sectional view.

FIG. 10 shows the details of that portion of the conductor 8 which defines the pole 6. This portion is a tubular member 12 having an open proximal end (nearer to the extension 5, not shown in FIG. 10) and a hollow conical distal portion 13 having an opening 14 in its tip for the passage of the conductor 9. The distal end of the conductor 8 is convoluted around the conductor 9 in the interior of the tubular member 12 and the wire in the insulating sheath 8a of the conductor 8 is electrically connected with the tubular member 12 but is insulated from the wire of the conductor 9. The sheath 8a terminates (at 15) in the interior of the tubular member 12, and the sheath 9a of the conductor 9 terminates (at 15') at the radially expanded strands 11 which define the pole 7. The hollow conical portion 13 of the tubular member 12 preferably clampingly engages the insulating sheath 9a so as to ensure that the conductor 9 can pull the tubular member 12 into the heart wall by way of the channel which is formed by the needle 3 for the radially deformable strands 11 defining the pole 7 as well as for the pole 6 which is defined by the tubular member 12. It will be noted that penetration of the needle 3 into the heart wall and the extraction of such needle from the heart 2 are automatically followed by proper implantation of both poles (6 and 7) in a single operation and by making a single channel or tunnel through the heart wall.

The insulating sheath of the conductor 8 is indicated in FIG. 1 by a heavy solid line, and the insulating sheath of the conductor 9 is indicated by a much thinner solid line. This is intended to denote that one can readily discriminate between the two conductors 8 and 9 for the purpose of proper attachment to the conductor means in the extension 5. For example, the average diameter of the conductor 9 can be actually less than the average diameter of the conductor 8. Alternatively, or in addition thereto, the color and/or texture of the sheath 9a can deviate from that of the sheath 8a to even more readily distinguish between the two conductors.

The feature that the conductor of a surgical electrode can be provided with a radially deformable portion which defines a pole of variable width can be utilized in the improved multipolar electrode 1 as well as in unipolar electrodes which comprise a single conductor and hence a single pole with a needle attached to the distal end of the single conductor. Such unipolar electrodes also exhibit the advantage that those portions of their conductors which define the poles tend to expand subsequent to implantation in the body of a patient to thus establish a highly desirable pronounced contact with the surrounding tissue. The tendency of the conductor portion which defines the radially deformable pole to expand subsequent to completion of the implanting step reduces the likelihood of undesirable migration of the pole in the body of the patient.

An important advantage of the improved multipolar electrode is its simplicity and its ability to implant both poles in a single operation and with little loss in time. Such electrode can be used as a temporary lead for cardiac pacing or monitoring purposes, i.e., to transmit stimuli or to monitor the functioning of a body organ. Another important advantage of the electrode is that it ensures the retention of the poles 6 and 7 at a preselected optimum distance from each other. With reference to FIG. 10, this is achieved in a simple and inexpensive way by ensuring that the insulating sheath 9a of the conductor 9 cannot slide relative to the tubular member 12 which defines the pole 6 of the conductor 8.

The establishment and retention of a certain distance between the poles 6 and 7 is desirable and advantageous because this reduces the likelihood of a short circuit as a result of movements of the heart in which the poles 6 and 7 are implanted. Still further, the electrode can utilize readily available and most satisfactory needles for predictable implantation of the poles 6 and 7 with a minimum of damage to the organ in which the poles are implanted. The number of punctures by the wall of the organ is reduced in half because both poles can be implanted in a single operation. The same applies for the number of punctures in the body for the purpose of introducing the needle into the thorax prior to penetration into the heart wall. Consequently, the duration of a surgery which is performed to implant the two poles in the myocardium is reduced to a fraction of the presently required time. Still further, simultaneous implantation of two poles which are compelled to remain at an optimum distance from each other automatically entails a more reliable anchoring of the poles in optimum positions.

The fact that the width of that portion of the conductor 9 which defines the pole 7 is increased by actually moving the strands of a multiple-strand wire apart at a desired distance from the pole 6 is of no consequence since the electrode 1 is not intended to be reused. On the other hand, the widening or enlargement of the pole-forming portion or portions 11 of the conductor 9 is simpler and less expensive than the application to the conductor 9 of discrete separately produced anchoring means which are intended to prevent migration of the pole 7 in the tissue. Such anchoring means are often used on electrodes for intravenous implantation in the heart. The widening of the conductor portion which defines the pole 7 automatically entails an enlargement of the surface-to-surface contact with the surrounding tissue which is desirable and advantageous for the aforediscussed reasons, particularly because it enhances stimulation of the heart by lowering the threshold of excitation.

The feature that the two poles are invariably held at an optimum distance from each other and from the needle 3 is desirable and advantageous for the aforediscussed reasons and constitutes a highly important improvement over conventional unipolar electrodes which must be implanted in pairs. Short circuiting of pairs of conventional unipolar electrodes is especially likely to occur if not only the atrium but also the ventricle of the heart must receive two poles i.e., if a total of four unipolar electrodes must be implanted in the cardium.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of our contribution to the art and, therefore, such adaptations should and are intended to be comprehended within the meaning and range of equivalence of the appended claims.

We claim:

1. A temporary lead for insertion in the body, particularly for cardiac pacing or monitoring purposes, comprising first conductor means including a first elongated conductor having a first proximal end and a first distal end, said first conductor means further including a first electrode in the region of said first distal end and electrically connected with said first conductor, and said first electrode having a width which exceeds the average width of said first conductor and being radially expandable and contractible; second conductor means including a second elongated conductor isulated from and extending along said first conductor, said second conductor having a second proximal end and a second distal end, and said second conductor means further including a second electrode in the region of said second distal end and electrically connected with said second conductor, said second electrode being spaced from said first electrode and being disposed between the latter and said proximal ends; and a needle connected with said electrodes and arranged to effect simultaneous introduction thereof into the body.

2. The lead of claim 1, wherein said needle is a curved surgical needle.

3. The lead of claim 1, further comprising an extension connected with the proximal ends of said conductors.

4. The lead of claim 1, wherein said first electrode is defined by a deformable portion of said first conductor.

5. The lead of claim 4, wherein said deformable portion of said first conductor has an undulate shape.

6. The lead of claim 4, wherein said deformable portion of said first conductor has a helical shape.

7. The lead of claim 4, wherein said deformable portion of said first conductor is zig-zag shaped.

8. The lead of claim 4, wherein said deformable portion of said first conductor includes a plurality of strands which are normally spaced apart from each other.

9. The lead of claim 8, wherein at least one of said strands has an undulate shape.

10. The lead of claim 8, wherein at least one of said strands is zig-zag shaped.

11. The lead of claim 8, wherein at least one of said strands has a helical shape.

12. The lead of claim 1, wherein said second electrode is defined by a tubular member and said first conductor extends through and beyond said tubular member.

13. The lead of claim 12, wherein said second distal end is convoluted around said first conductor in the interior of said tubular member.

14. The lead of claim 12, wherein said tubular member is insulated from said first conductor.

15. The lead of claim 12, wherein said tubular member has an open proximal end and a conical portion at the distal end thereof, said first conductor extending through and beyond the conical portion of said tubular member.

16. The lead of claim 1 comprising means for facilitating discrimination between said conductors.

17. The lead of claim 1, wherein said needle is secured to said first distal end.

18. The lead of claim 17, wherein said needle is separable from said distal end.

19. The lead of claim 1, wherein said first conductor comprises at least one flexible strand provided with an electrically insulating sheath, said one flexible strand projecting from said sheath in the region of said first distal end so that a portion of said one flexible strand is bare, and said bare portion of said one flexible strand at least in part constituting said first electrode.

20. The lead of claim 3, wherein said extension is needle-like.

21. The lead of claim 12, said second conductor comprising at least one strand provided with an electrically insulating sheath; and wherein said one strand projects from said sheath in the region of said second distal end so that at least a portion of said second distal end is bare, said bare portion of said second distal end being located inside said tubular member.

22. The lead of claim 12, wherein said tubular member clamps said first conductor.

* * * * *